(12) United States Patent
Hanley et al.

(10) Patent No.: US 9,888,964 B2
(45) Date of Patent: Feb. 13, 2018

(54) SIDE-FIRING LASER FIBER WITH GLASS FUSED REFLECTOR AND CAPILLARY AND RELATED METHODS

(71) Applicant: Boston Scientific Scimed, Inc., Maple Grove, MN (US)

(72) Inventors: Brian M. Hanley, Framingham, MA (US); Jessica Hixon, Miami, FL (US); Christopher L. Oskin, Grafton, MA (US); Edward Sinofsky, Dennis, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/148,382

(22) Filed: Jan. 6, 2014

(65) Prior Publication Data

US 2014/0309627 A1    Oct. 16, 2014

Related U.S. Application Data

(63) Continuation of application No. 12/468,364, filed on May 19, 2009, now abandoned.

(Continued)

(51) Int. Cl.
*A61B 18/24* (2006.01)
*A61B 18/22* (2006.01)

(52) U.S. Cl.
CPC ............ *A61B 18/24* (2013.01); *A61B 18/22* (2013.01); *A61B 2018/2272* (2013.01)

(58) Field of Classification Search
CPC ............ A61B 18/24; A61B 2018/2244; A61B 2018/2272

(Continued)

(56) References Cited

U.S. PATENT DOCUMENTS 4,147,409 A * 4/1979 Apfel ............................. 359/584
4,662,368 A * 5/1987 Hussein ................. A61B 18/20
606/15

(Continued)

FOREIGN PATENT DOCUMENTS

EP    0 400 802 A2    12/1990
EP    0 610 991 A2    8/1994

OTHER PUBLICATIONS

International Search Report and Written Opinion for International Application No. PCT/US2009/044462, dated Oct. 6, 2009, 11 pages.

*Primary Examiner* — Nathan J Jenness
(74) *Attorney, Agent, or Firm* — Bookoff McAndrews, PLLC

(57) ABSTRACT

A method and an apparatus according to an embodiment of the invention includes a reflector and an optical fiber end portion disposed within a capillary for use in side-firing optical fibers. The reflector surface can be coated with a multilayer dielectric coating to increase the amount of side-fired laser energy. An outer member or cap can be used to protect the capillary when being inserted through a catheter or endoscope. The endoscope is then at least partially inserted into a patient's body to provide laser-based medical treatment. Multiple grooves can be defined on an outer surface of the optical fiber buffer layer to increase the surface area and improve the mechanical strength of the coupling between the optical fiber and the capillary. In some embodiments, the outer member or cap can also be coupled to the grooved surface portion of the optical fiber buffer layer.

18 Claims, 9 Drawing Sheets

Related U.S. Application Data

(60) Provisional application No. 61/054,285, filed on May 19, 2008.

(58) Field of Classification Search
USPC .................................................. 606/15, 16
See application file for complete search history.

(56) References Cited

U.S. PATENT DOCUMENTS

| | | | |
|---|---|---|---|
| 5,163,935 A | 11/1992 | Black et al. | |
| 5,242,438 A | 9/1993 | Saadatmanesh et al. | |
| 5,354,294 A | 10/1994 | Chou | |
| 5,366,456 A | 11/1994 | Rink et al. | |
| 5,431,647 A | 7/1995 | Purcell et al. | |
| 5,437,660 A * | 8/1995 | Johnson et al. | 606/15 |
| 5,486,171 A | 1/1996 | Chou | |
| 5,537,499 A | 7/1996 | Brekke | |
| 5,562,657 A * | 10/1996 | Griffin | A61B 18/245 606/13 |
| 5,649,924 A | 7/1997 | Everett et al. | |
| 5,772,657 A | 6/1998 | Hmelar et al. | |
| 5,833,683 A | 11/1998 | Fuller et al. | |
| 6,096,028 A | 8/2000 | Bahmanyar et al. | |
| 6,102,905 A * | 8/2000 | Baxter et al. | 606/15 |
| 6,296,608 B1 | 10/2001 | Daniels et al. | |
| 6,445,939 B1 | 9/2002 | Swanson et al. | |
| 6,522,827 B1 | 2/2003 | Loeb et al. | |
| 6,554,824 B2 | 4/2003 | Davenport et al. | |
| 6,565,555 B1 | 5/2003 | Ryan et al. | |
| 6,575,965 B1 | 6/2003 | Fitch et al. | |
| 6,615,072 B1 | 9/2003 | Izatt et al. | |
| 6,620,154 B1 | 9/2003 | Amirkhanian et al. | |
| 6,891,984 B2 | 5/2005 | Petersen et al. | |
| 7,108,692 B2 | 9/2006 | Frenz et al. | |
| 7,169,140 B1 | 1/2007 | Kume | |
| 7,492,987 B2 | 2/2009 | Yeik et al. | |
| 2006/0282068 A1 | 12/2006 | Griffin et al. | |
| 2007/0179485 A1* | 8/2007 | Yeik | A61B 18/24 606/15 |

* cited by examiner

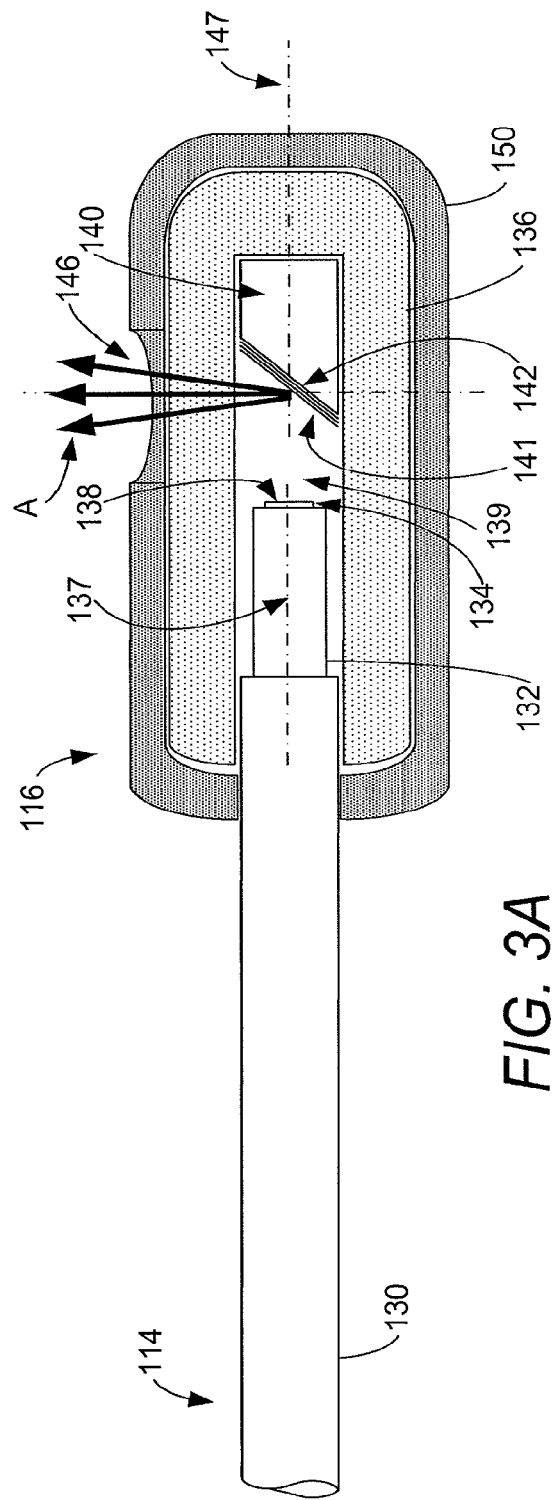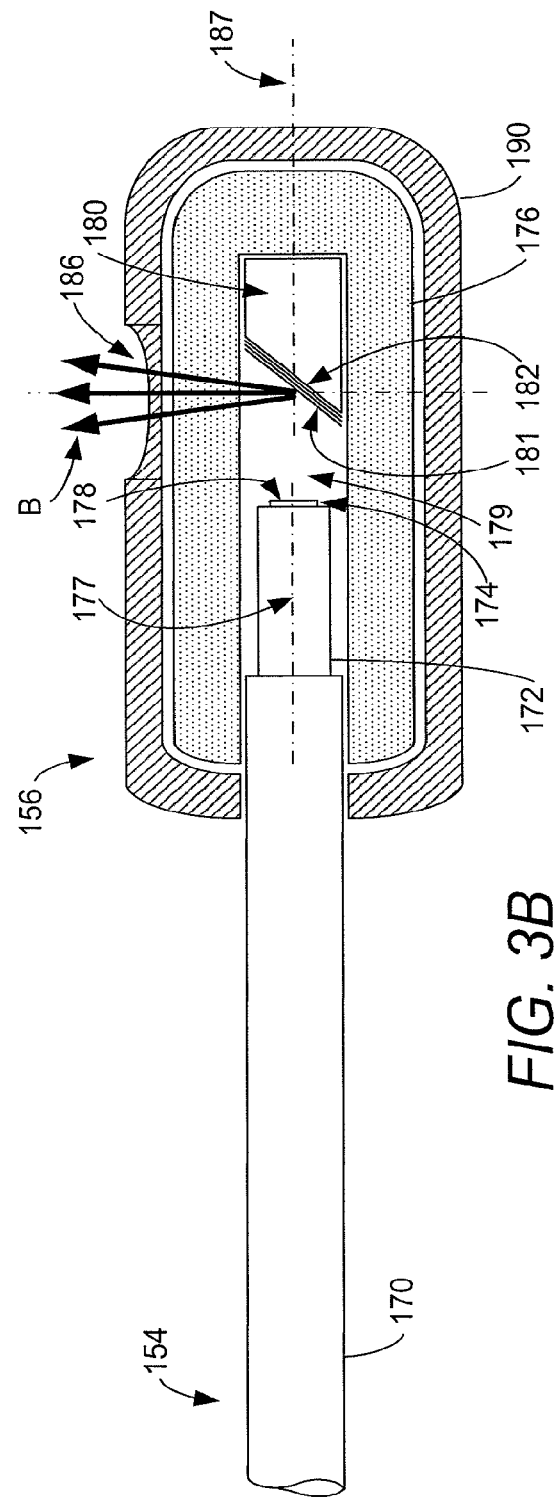
FIG. 3A
FIG. 3B

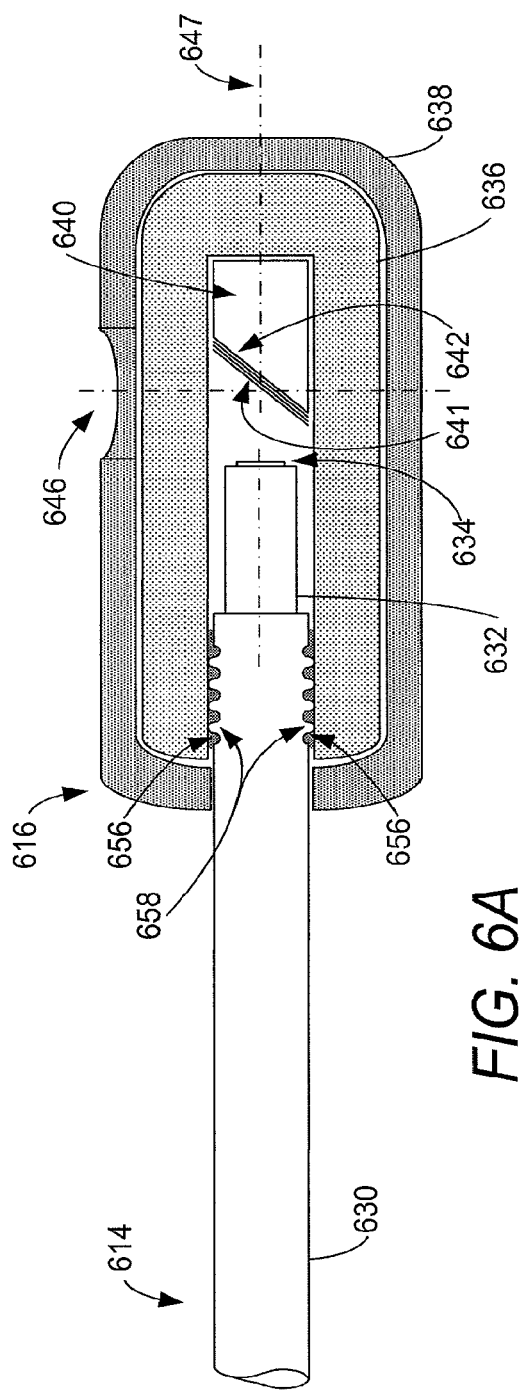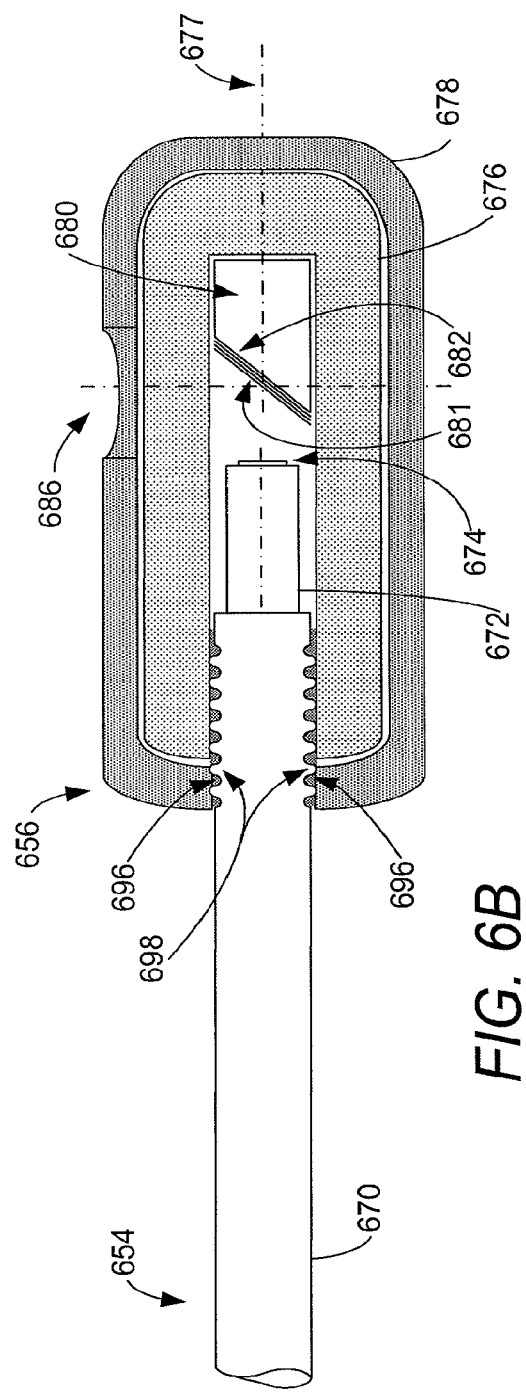

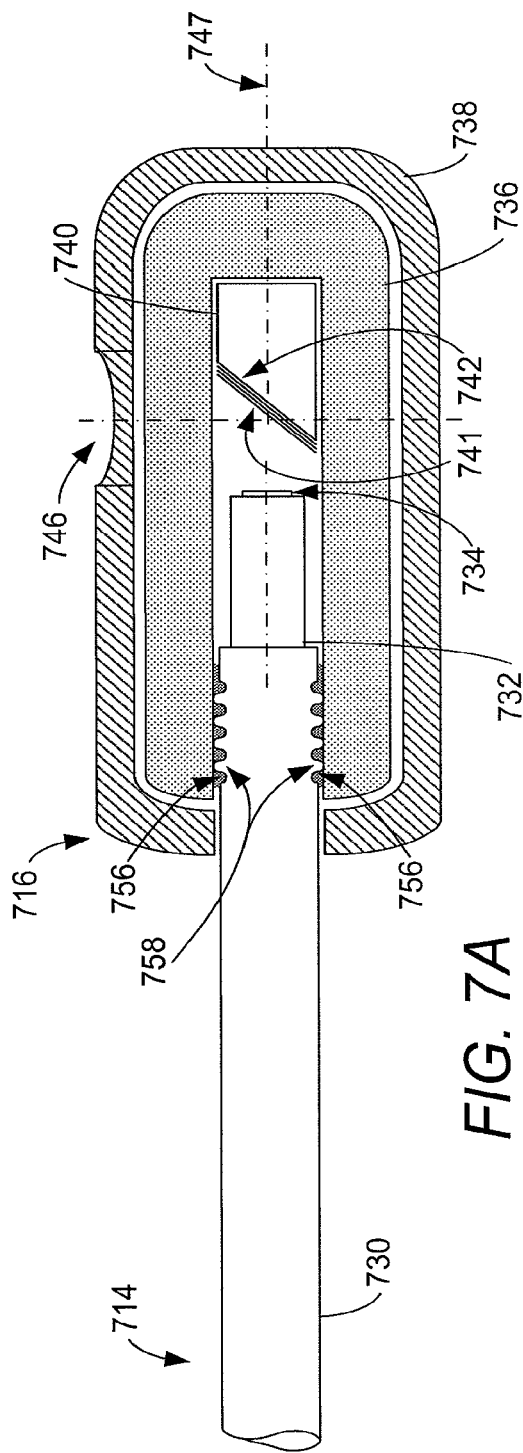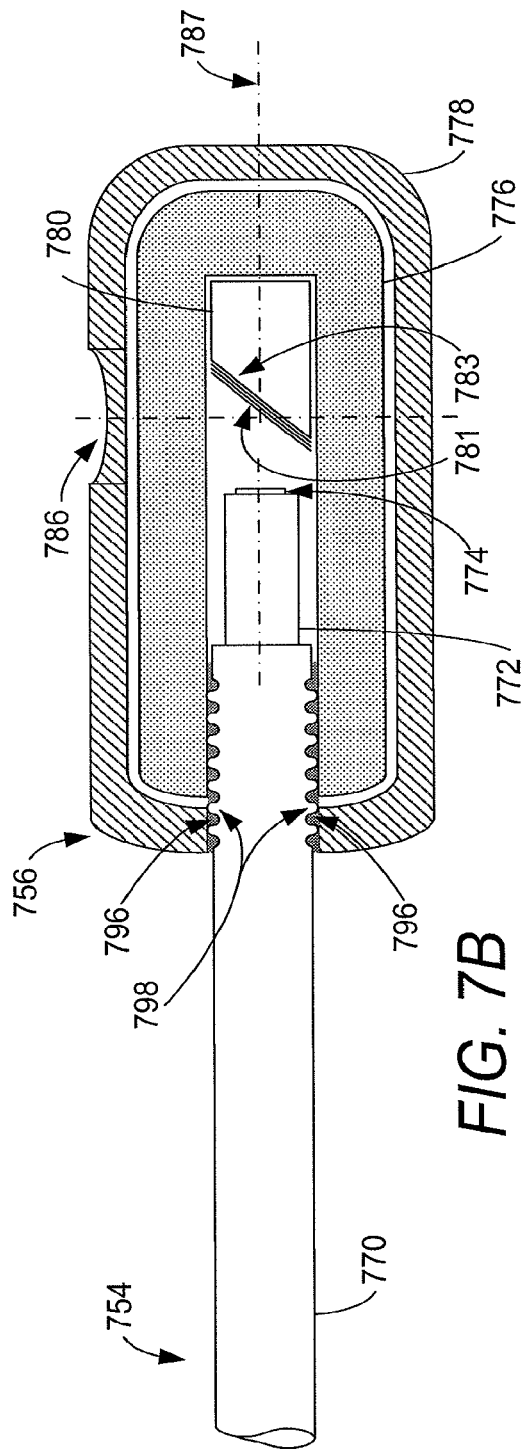

SIDE-FIRING LASER FIBER WITH GLASS FUSED REFLECTOR AND CAPILLARY AND RELATED METHODS

RELATED APPLICATION

This application is a continuation of U.S. patent application Ser. No. 12/468,364, filed May 19, 2009, which claims priority to and the benefit of U.S. Provisional Application No. 61/054,285, filed on May 19, 2008, both of which are incorporated herein by reference in its their entirety.

BACKGROUND

The invention relates generally to medical devices and more particularly to side-firing optical fibers and methods for using such devices.

Laser-based surgical procedures using side-firing optical fibers can provide a medical practitioner with more control when applying laser energy to the appropriate treatment area. Passing the distal end portion of the optical fiber through an endoscope during surgery, however, may damage, scratch, degrade, and/or deform the distal end portion of the optical fiber. To protect the optical-fiber end portion, a capillary and/or a metal cap or cannula, usually made of surgical grade stainless steel, can be placed over the optical-fiber end portion. Once the distal end portion of the optical fiber is properly positioned for treatment, the laser energy can be applied to the target area.

During use of the device, a portion of the laser energy can leak from the distal end portion of the optical fiber, reducing the efficiency with which laser energy is delivered to the treatment area and/or increasing overheating of the metal cap that is typically used to protect the optical fiber. Cooling of the device may be needed to operate at a safe temperature. In some instances, the overheating that can occur from the laser energy leakage can affect the mechanical and/or optical properties of the optical-fiber end portion, the capillary and/or the metal cap. In other instances, the overheating that can occur from the laser energy leakage can be sufficiently severe to damage the optical-fiber end portion, the capillary and/or the metal cap.

Overheating can also occur from the use of reflectors such as metallic reflectors or tips configured to redirect or bend an optical beam about 90 degrees from its original propagation path based on total internal reflection (TIR). Because metallic reflectors do not reflect 100% of the optical beam, the energy associated with the non-reflected portion of the optical beam can be absorbed by the metallic reflector and the metallic reflector can self heat. For TIR-based tips, a portion of the optical beam can leak through and heat up a protective metal cap positioned on a distal end of the tip. Furthermore, the glass capillary tubing that is generally used on the TIR-based tips can become damaged as tissue is ablated and impact against the glass capillary tubing.

Thus, a need exists for optical-fiber end portions that can increase side-fired laser energy, increase device longevity, increase transmission efficiency, reduce overheating, and/or increase patient safety.

SUMMARY

An apparatus includes a reflector and an optical fiber end portion disposed within a capillary for use in side-firing optical fibers. The reflector surface can be coated with a multilayer dielectric coating. An outer member or cap can be used to protect the capillary when being inserted through a catheter or endoscope. The endoscope is at least partially inserted into a patient's body to provide laser-based medical treatment. Multiple grooves can be defined on an outer surface of the optical fiber buffer layer to increase the surface area and improve the mechanical strength of the coupling between the optical fiber and the capillary. In some embodiments, the outer member or cap can also be coupled to the grooved surface portion of the optical fiber buffer layer.

BRIEF DESCRIPTION OF THE DRAWINGS

FIG. 3A is a cross-sectional view of a side-firing optical fiber with a capillary and a protective cap, according to an embodiment of the invention.

FIG. 3B is a cross-sectional view of a side-firing optical fiber with a capillary and a protective cap, according to another embodiment of the invention.

FIGS. 6A-6B are cross-sectional views of a grooved buffer layer surface coupled to a capillary with an optically-transmissive protective cap, according to embodiments of the invention.

FIGS. 7A-7B are cross-sectional views of a grooved buffer layer surface coupled to a capillary with an optically-opaque protective cap, according to embodiments of the invention.

DETAILED DESCRIPTION

Figure 1:
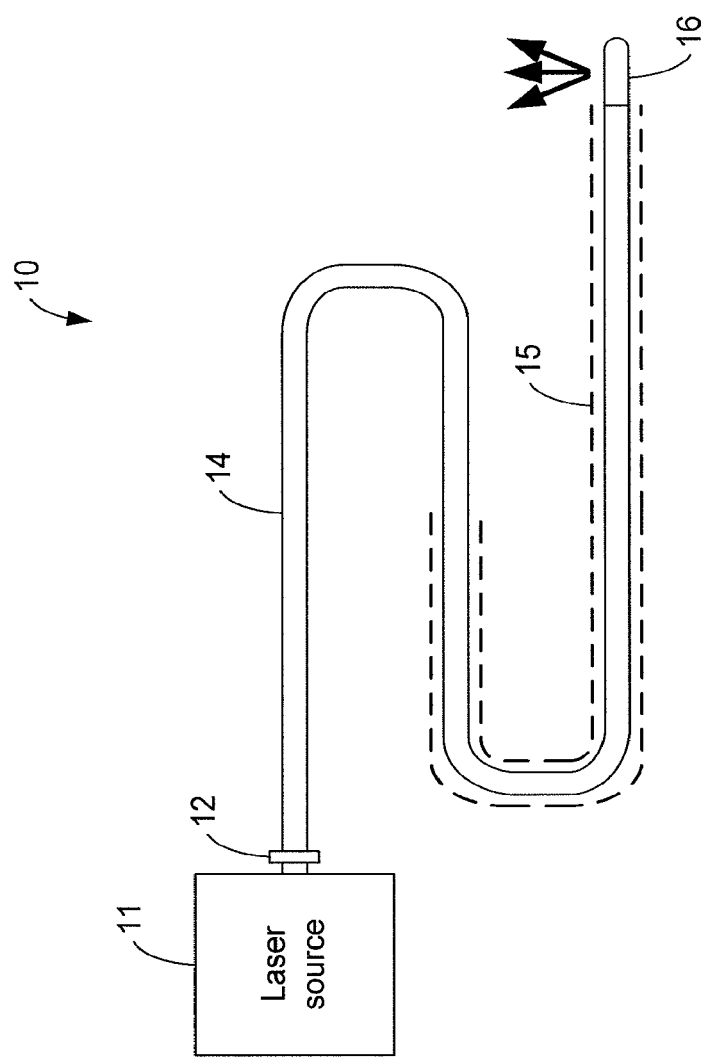
FIG. 1 is a schematic representation of a side-firing optical fiber system according to an embodiment of the invention.

The devices and methods described herein are generally related to the use of side-firing optical fibers within the body of a patient. For example, the devices and methods are suitable for use in treating symptoms related to an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists and once the prostate begins to enlarge, it often continues, unless medical treatment is initiated.

Patients who develop symptoms associated with BPH generally need some form of treatment. When the prostate gland is mildly enlarged, research studies indicate that early treatment may not be needed because the symptoms clear up without treatment in as many as one-third of cases. Instead of immediate treatment, regular checkups are recommended. Only if the condition presents a health risk or the symptoms result in major discomfort or inconvenience to the patient is treatment generally recommended. Current forms of treatment include drug treatment, minimally-invasive therapy, and surgical treatment. Drug treatment is not effective in all cases and a number of procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing side-firing optical fibers and high-power lasers have been used to remove obstructing prostate tissue. In these procedures, a doctor passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization and in most cases the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nm. This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cc (cubic centimeters). Laser-based surgical procedures, such as HoLAP and HoLEP, are becoming more preferable because they produce similar results to those obtained from TURP surgery while having fewer complications and requiring shorter hospital stay, shorter catheterization time, and shorter recovery time.

An optical fiber system as described herein can be used to transmit laser energy from a laser source to a target treatment area within a patient's body. The optical fiber system can include a laser source and an optical fiber. One end of the optical fiber can be coupled to the laser source while the other end of the optical fiber, the distal end portion (e.g., the end with a side-firing or laterally-firing portion), can be inserted into the patient's body to provide laser treatment. The distal end portion can include a capillary and a reflective member or reflector within the capillary. An angled or beveled end surface of the reflector disposed within the capillary can redirect laser energy in a lateral direction for side-firing transmission of laser energy to the area of treatment. The angled end surface of the reflector can include, for example, a multilayer dielectric coating. The multilayer dielectric coating can be configured to reflect a portion of the optical beam (e.g., laser beam) from the optical fiber that impinges on the end surface of the reflector at a less glancing angle and would not otherwise be totally internally reflected. In one embodiment, multiple grooves can be defined on an outer surface of the optical fiber buffer layer to produce a grooved surface portion that is used to improve the mechanical strength of the coupling between the optical fiber and the capillary. In other embodiments, a cap used to protect the capillary can also be coupled to a portion of the grooved surface of the optical fiber buffer layer.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., medical practitioner, medical practitioner, nurse, technician, etc.) who would insert the medical device into the patient, with the tip-end (i.e., distal end) of the device inserted inside a patient's body. Thus, for example, the optical fiber end inserted inside a patient's body would be the distal end of the optical fiber, while the optical fiber end outside a patient's body would be the proximal end of the optical fiber.

FIG. 1 is a schematic representation of a side-firing optical fiber system according to an embodiment of the invention. An optical fiber side-firing system 10 can include a laser source 11, an optical coupler 12, an optical fiber 14, and an optical-fiber distal end portion 16. The optical fiber side-firing system 10 also includes a suitable catheter or endoscope 15 for inserting the optical-fiber distal end portion 16 into a patient's body. The laser source 11 can include at least one laser that can be used to generate laser energy for surgical procedures. The laser source 11 can include a Ho:YAG laser, for example. The laser source 11 can include at least one of a neodymium-doped:YAG (Nd:YAG) laser, a semiconductor laser diode, or a potassium-titanyl phosphate crystal (KTP) laser, for other examples. In some embodiments, more than one laser can be included in the laser source 11 and more than one laser can be used during a surgical procedure. The laser source 11 can also have a processor that provides timing, wavelength, and/or power control of the laser. For example, the laser source 11 can include mechanisms for laser selection, filtering, temperature compensation, and/or Q-switching operations.

The optical fiber 14 can be coupled to the laser source 11 through the optical coupler 12. The optical coupler 12 can be an SMA connector, for example. The proximal end of the optical fiber 14 can be configured to receive laser energy from the laser source 11 and the distal end of the optical fiber 14 can be configured to output the laser energy through the optical-fiber distal end portion 16. The optical fiber 14 can include, for example, a core, one or more cladding layers about the core, a buffer layer about the cladding, and a jacket. The core can be made of a suitable material for the transmission of laser energy from the laser source 11. In some embodiments, when surgical procedures use wavelengths ranging from about 500 nm to about 2100 nm, the core can be made of silica with a low hydroxyl (OH⁻) ion residual concentration. An example of using low hydroxyl (low-OH) fibers in medical devices is described in U.S. Pat. No. 7,169,140 to Kume, the disclosure of which is incorporated herein by reference in its entirety. The core can be multi-mode and can have a step or graded index profile. The cladding can be a single or a double cladding that can be made of a hard polymer or silica. The buffer can be made of a hard polymer such as Tefzel®, for example. When the optical fiber includes a jacket, the jacket can be made of Tefzel®, for example, or can be made of other polymers.

The endoscope 15 can define one or more lumens. In some embodiments, the endoscope 15 includes a single lumen that can receive therethrough various components such as the optical fiber 14. The endoscope 15 has a proximal end configured to receive the optical-fiber distal end portion 16 and a distal end configured to be inserted into a patient's body for positioning the optical-fiber distal end portion 16 in an appropriate location for a laser-based surgical procedure. For example, to relieve symptoms associated with BPH, the endoscope 15 can be used to place the optical-fiber distal end portion 16 at or near the enlarged portion of the prostate gland. The endoscope 15 includes an elongate portion that can be flexible to allow the elongate portion to be maneuvered within the body. The endoscope 15 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel (not shown) is defined by the endoscope 15 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 15, for example, and coupled to an optical fiber that can be disposed within a lumen of the endoscope 15. Such an embodiment allows a medical practitioner to view the interior of a patient's body through the eyepiece.

The optical-fiber distal end portion 16 can include one or more members, elements, or components that can individually or collectively operate to transmit laser energy in a lateral direction offset from a longitudinal axis or centerline of the distal end of the optical fiber core. In an embodiment, the optical-fiber distal end portion 16 can have a reflector or reflective member with a multilayer dielectric coating on an angled surface for side-firing laser energy during a surgical procedure. Such a multilayer dielectric coating can be configured to have a high reflectance value (e.g., R>99.9%) at the laser operating wavelength and/or at the desired angle of incidence.

Figure 2:
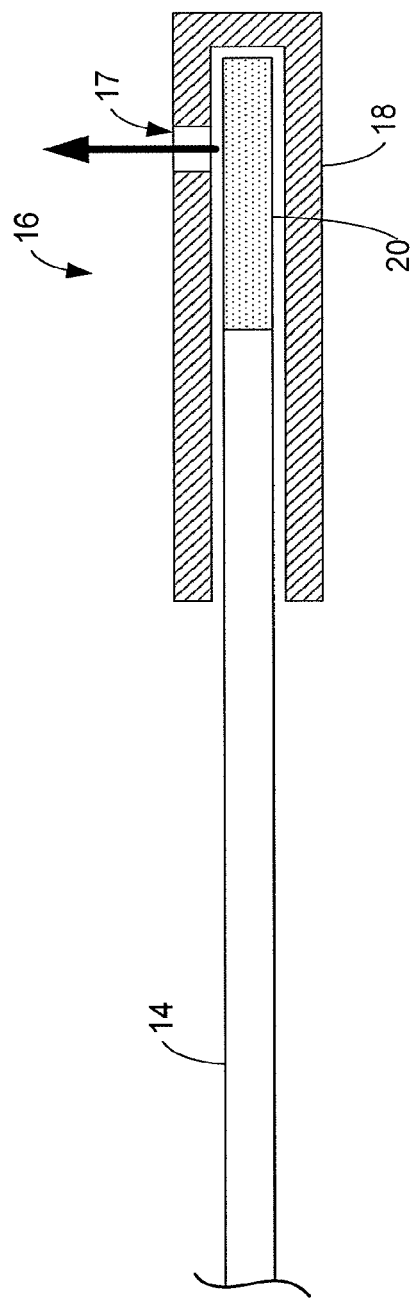
FIG. 2 is a cross-sectional view of an optical-fiber distal end portion according to an embodiment of the invention.

FIG. 2 is a cross-sectional view of an optical-fiber distal end portion according to an embodiment of the invention. The optical-fiber distal end portion 16 can include an inner portion 20 and surrounded by an outer portion 18. The outer portion 18 can include a high-profile member such as, for example, a metal or ceramic cover or cap. The cover or cap is generally made of surgical grade stainless steel or other materials with like properties. In some instances, it can be desirable to have the cap made of a ceramic material (e.g., alumina) because certain ceramics can offer stable characteristics at high-temperatures and/or have a high reflectance value at the laser operating wavelength. The outer portion 18 can provide protection to the optical-fiber distal end portion 16. In some embodiments, the outer portion 18 can include a low-profile cover (e.g., a coating or a sleeve).

The outer portion 18 can include a window or transmissive portion 17 through which laterally-redirected or side-fired laser energy can be transmitted for surgical treatment. For example, when the outer portion 18 is made of an opaque material, a window can be defined after removing at least a portion of the opaque material. In another example, when the outer portion 18 is made of an optically-transmissive material, laser energy can be transmitted or sent through the outer portion 18. In some embodiments, the optically-transmissive material can be treated thermally, optically, mechanically, and/or chemically to improve its structural and/or optical characteristics such that laser energy can be delivered more effectively to the target area. For example, the optically-transmissive material can be thermally treated during manufacturing using a $CO_2$ laser.

The inner portion 20 can include one or more members, components, and/or devices to redirect laser energy. For example, the inner portion 20 can include a capillary or capillary tube. The capillary can be made of, for example, at least one of silica, sapphire, and/or other like materials. In one embodiment, the inner portion 20 can include a distal end portion of the core of the optical fiber 14 disposed within a capillary. As described below in more detail, the inner portion 20 can also include reflective members and/or mirrors that can be used to redirect laser energy to provide side-firing operations.

FIG. 3A is a cross-sectional view of a side-firing optical fiber with a capillary and a protective cap, according to an embodiment of the invention. The side-firing optical-fiber distal end portion 116 can include a reflective member 140 disposed within a capillary 136. A distal end portion of a buffer layer 130, a distal end portion of a cladding layer 132, and an optical-fiber-core distal end portion 134 can be disposed within the capillary 136. The optical-fiber-core distal end portion 134 can include a core-end surface 138 that is substantially perpendicular to a longitudinal axis or centerline 137 of the optical-fiber-core end portion 134. In some instances, the distal end of the cladding layer 132 can extend to the distal end of the optical-fiber-core end portion 134 (e.g., the polished end). Laser energy A transmitted through the optical fiber 114 can exit via the core-end surface 138 and redirected at the reflector 140.

The capillary 136 can be disposed within a low-profile protective cap or outer member 150 that is made of an optically-opaque material. In one embodiment, the outer member 150 can be made of a polymer-based coating or sleeve, for example. A window or transmissive portion 146 on the outer member 150 may be defined through which the laser energy A can be transmitted during a surgical procedure. The window 146 can be offset from a longitudinal axis or centerline 147 of the distal end portion of the capillary 136. The capillary 136 can be made of an optically-transmissive material such as, for example, sapphire. The capillary 136 and/or the outer member 150 can be coupled to an outer surface of the distal end portion the buffer layer 130, for example. Because of the size, shape, and/or weight of the capillary 136 and/or the outer member 150, the overlap area between the capillary 136 and the outer surface of the buffer layer 130 may need to be sufficiently large to provide mechanical stability to the joint or coupling.

The reflector 140 can include a proximal end surface 142 that is angled relative to a longitudinal axis or centerline 147 of distal end portion of the capillary 136. In some embodiments, the longitudinal axis 147 of the capillary 136 can be substantially parallel to and co-axial with the longitudinal axis 137 of the optical-fiber-core end portion 134. The reflector 140 can be made of various materials such as, for example, a polymer, a glass, a metal, and/or a ceramic. The optical, thermal, and/or mechanical properties of a material and/or combination of materials can be considered when determining the appropriate material, shape, and/or size for the reflector 140. For example, substantially matching thermal expansion coefficients for the reflector 140 and the capillary 136 can reduce the effect that overheating may have on the device. Moreover, material selection may also depend on the mechanism by which the reflector 140 is to be fixed within the capillary 136. For example, a glass-based reflector 140 and a glass-based capillary 136 can be joined or coupled through a fusion process that uses a $CO_2$ laser during manufacturing to perform the fusion operation. In this regard, reducing or minimizing the formation of bubbles, air gaps, and/or defects during the fusion process can produce better matching of optical, thermal and/or mechanical properties. In another example, a polymer-based reflector 140 and a glass-based capillary 136 may be coupled using an appropriate adhesive.

The angled surface 142 can be configured to produce reflection of laser energy that is transmitted through the optical-fiber-core end portion 134 to laterally redirect the laser energy. The angled surface 142 can be used to redirect laser energy in a lateral direction offset from the longitudinal axis or centerline 147 of the distal end portion of the capillary 136. By determining an appropriate angle or configuration for the angled surface 142, the laser energy A can be transmitted in a lateral direction that is appropriate for laser-based surgical procedures. For example, a 45 degree angle of incidence can result in the laser or optical beam being laterally reflected at an angle of about 90 degrees from the longitudinal axis of the distal end portion of the optical fiber.

The angle of the angled surface 142 can be determined based on at least one of several parameters. For example, the angle can be configured based on the wavelength of the laser energy A, the exit or output location for the laser energy A, and/or the optical properties of the capillary 136 and/or the reflector 140. Moreover, the optical properties of a volume or region 139 that remains within the inner portion of the capillary 136 after the disposing of the distal end portion of the optical fiber 114 and the reflector 140 can also be used in determining an appropriate angle for the angled surface 142. For example, the region 139 can include a gas, a liquid, and/or a solid to improve reflection at the angled surface 142. In other words, the use of a gas, liquid, and/or solid can have an index of refraction different than air. This index of refraction can alter the amount of laser energy that is reflected at the angled surface 142.

As shown in FIG. 3A, a multilayer dielectric coating 141 can be disposed on the angled surface 142. The multilayer dielectric coating 141 can be used to improve the reflection efficiency of the angled surface 142 over a wider range of angles associated with the laser beam propagation through the optical fiber. The high reflectivity and low optical absorption of multilayer dielectric coatings can reduce the device operating temperature and/or reduce the amount of cooling that may be used to operate the device at a safe temperature.

The multilayer dielectric coating 141 can be made of multiple dielectric layers that collectively and efficiently operate to reflect laser energy. A dielectric layer can be made of a alternating layers of $SiO_2$ (silica) and $TiO_2$ (titanium dioxide or titania), for example. The multilayer dielectric coating 141 can include alternating layers of two or more materials each with a different dielectric constant. In some embodiments, the multilayer dielectric coatings can be configured to operate as a ¼ wavelength mirror in which sets of two alternating layers are used and each layer has an optical thickness that is ¼ the wavelength of the laser energy. The multilayer dielectric coating 141 can be deposited using any of multiple deposition techniques, such as electron beam or ion beam deposition, for example. The multilayer dielectric coating 141, the reflector 140, and/or the optical-fiber-core end portion 134 can be collectively configured to redirect the laser energy A transmitted from the core-end surface 138 in a side-fired direction that passes through the capillary 136 and through the window 146.

FIG. 3B is a cross-sectional view of a side-firing optical fiber with a capillary and a protective cap, according to another embodiment of the invention. The side-firing optical-fiber distal end portion 156 can include a reflective member 180 disposed within a capillary 176. A distal end portion of a buffer layer 170, a distal end portion of a cladding layer 172, and an optical-fiber-core distal end portion 174 can be disposed within the capillary 176. The optical-fiber-core distal end portion 174 can include a core-end surface 178 that is substantially perpendicular relative to a longitudinal axis or centerline 177 of the optical-fiber-core distal end portion 174. Laser energy B transmitted through the optical fiber 154 can exit via the core-end surface 178 to be redirected at the reflector 180.

The capillary 176 can be disposed within a high-profile protective cap or outer member 190 that is made of an optically-opaque material. In one embodiment, the outer member 190 can be made of a metal such as, for example, surgical grade stainless steel. A window or transmissive portion 186 on the outer member 190 may be defined through which the laser energy B can be transmitted during a surgical procedure. The window 186 can be offset from a longitudinal axis or centerline 187 of the distal end portion of the capillary 176. As shown in FIG. 3B, the capillary 176 can be made of an optically-transmissive material such as, for example, sapphire. A multilayer dielectric coating 181 disposed on an angled surface 182, the reflector 180, and/or the optical-fiber-core distal end portion 174 can be collectively configured to redirect the laser energy B transmitted from the core-end surface 178 in a side-fired direction that passes through the capillary 176 and through the window 186.

Figure 4B:
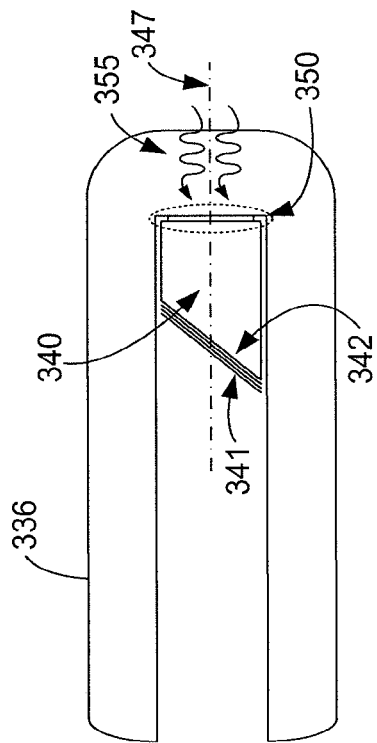
FIGS. 4A-4C are cross-sectional views of a capillary with a fused reflective member, according to embodiments of the invention.
Figure 4A:
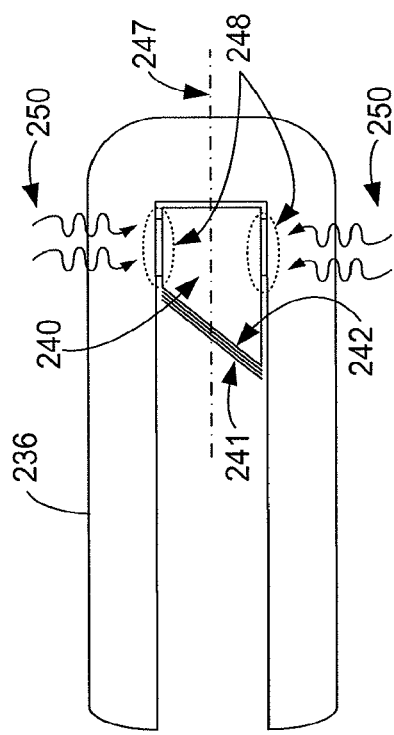
Figure 4C:
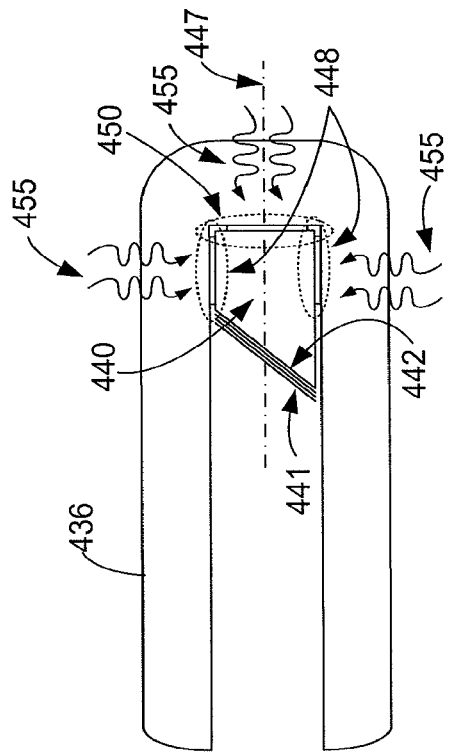

FIGS. 4A-4C are cross-sectional views of a capillary with a fused reflective member, according to embodiments of the invention. FIG. 4A shows a reflector 240 disposed within a capillary 236 and proximate to a distal end of an inner portion of the capillary 236. The proximal end surface 242 of the reflector 240 is angled relative to the longitudinal axis or centerline 247 of the distal end portion of the capillary 236. A multilayer dielectric coating 241 can be disposed on the angled surface 242.

The reflector 240 can be fixedly coupled to the capillary 236 through a fusion operation that produces an interface or fusion region 248. As shown in FIG. 4A, laser energy 250 from a $CO_2$ laser, for example, can be used during manufacture to fuse at least a portion of an outer surface of the reflector 240 to the inner portion of the capillary 236. The portion of the outer surface of the reflector 240 that is fused to the capillary 236 can be offset from the longitudinal axis or centerline 247. Reducing or minimizing the formation of bubbles, air gaps, and/or defects during the fusion process can produce better matching of optical, thermal and/or mechanical properties between the capillary 236 and the reflector 240.

In another embodiment, as shown in FIG. 4B, a reflector 340 can be disposed within a capillary 336 and proximate to a distal end of an inner portion of the capillary 336. The proximal end surface 342 of the reflector 340 is angled relative to the longitudinal axis or centerline 347 of the distal end portion of the capillary 336. A multilayer dielectric coating 341 can be disposed on the angled surface 342. The reflector 340 can be fixedly coupled to the capillary 336 through a fusion operation that produces an interface or fusion region 350. FIG. 4B shows the use of laser energy 355 to fuse at least a portion of a distal end surface or distal facing surface of the reflector 340 to the inner portion of the capillary 336. The distal end surface of the reflector 340 that is fused to the capillary 336 can be substantially perpendicular to the longitudinal axis 347.

FIG. 4C shows a reflector 440 disposed within a capillary 436 and proximate to a distal end of an inner portion of the capillary 436. The reflector 440 can be fixedly coupled to the capillary 436 through a fusion operation that produces an interface or fusion region 448 and a fusion region 450. Laser energy 455 can be used during manufacture to fuse at least a portion of a distal end surface of the reflector 440 and a portion of an outer surface of the reflector 440 to the inner portion of the capillary 436. The distal end surface of the reflector 440 that is fused to the capillary 436 can be substantially perpendicular to the longitudinal axis 447. The portion of the outer surface of the reflector 440 that is fused to the capillary 436 can be offset from the longitudinal axis or centerline 447.

Figure 5:
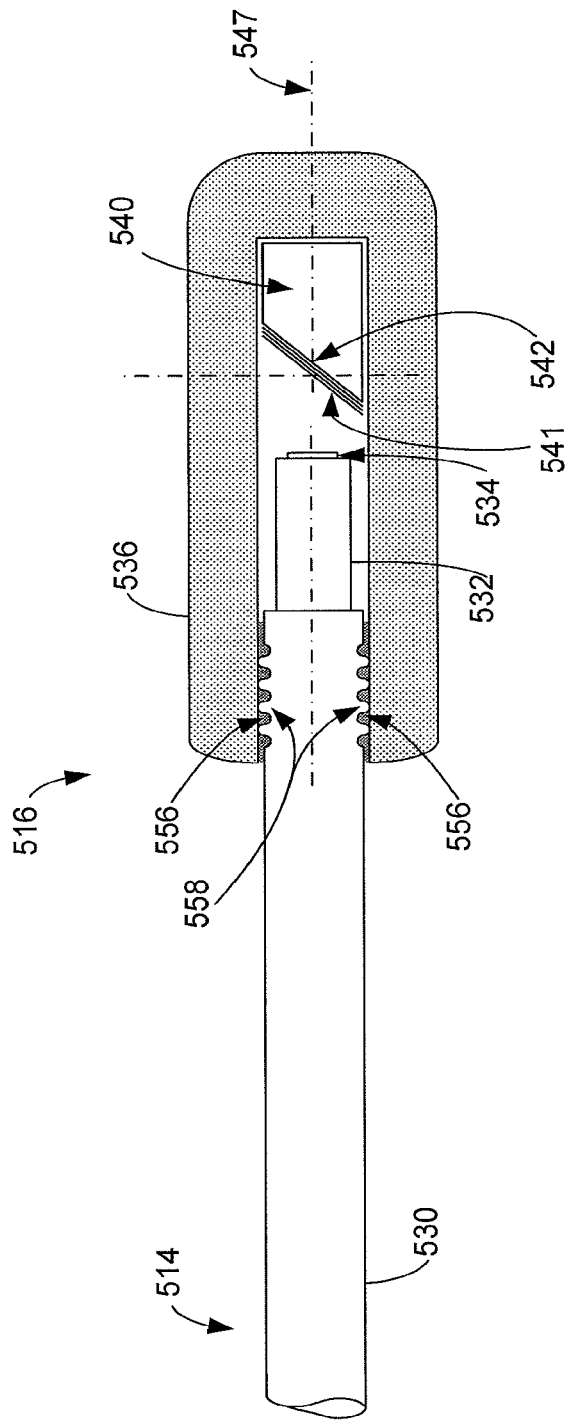
FIG. 5 is a cross-sectional view of a grooved buffer layer surface coupled to a capillary with a reflective member inside, according to an embodiment of the invention.

FIG. 5 is a cross-sectional view of a grooved buffer layer surface coupled to a capillary with a reflective member inside, according to an embodiment of the invention. The side-firing optical-fiber distal end portion 516 can include a reflective member 540 disposed within a capillary 536. A distal end portion of a buffer layer 530, a distal end portion of a cladding layer 532, and an optical-fiber-core distal end portion 534 can be disposed within the capillary 536. A multilayer dielectric coating 541 can be disposed on an angled surface 542 of the reflective member 540. A proximal end portion of an inner portion of the capillary 536 can be coupled to an outer surface of the distal end portion of the buffer layer 530.

Because of the size, shape, and/or weight of the capillary 536, the overlap area between the capillary 536 and an outer surface of the distal end portion of the buffer layer 530 may need to be sufficiently large to provide mechanical stability to the joint or coupling. In an embodiment, the production or definition of multiple grooves 558 in the outer surface of the buffer layer 530 increases the overlap area with the capillary 536 by increasing the total surface area of the outer surface of the buffer layer 530 that overlaps the capillary 536. The grooves 558 in the grooved surface portion of the buffer layer 530 can be made by, for example, a thermal process that defines an appropriate number, size, and/or spacing for the grooves 558. In one embodiment, the thermal process can include a applying a heated comb-like template to the surface of the buffer layer 530. In another embodiment, the thermal process can include using a laser, a metal ring, or a metal ring with protrusions to define the grooved surface portion of the buffer layer 530. An adhesive 556 can be applied to the grooved surface portion of the buffer layer 530 to couple the grooved surface to the inner portion of the capillary 536. The adhesive 556 can be selected at least partly based on the type of materials used for the buffer layer 530 and for the capillary 536.

FIGS. 6A-6B are cross-sectional views of a grooved buffer layer surface coupled to a capillary with an optically-transmissive protective cap, according to embodiments of the invention. FIG. 6A shows a side-firing optical-fiber 614 distal end portion 616 that includes a capillary 636 having a centerline 647 and disposed within a high-profile protective cap or outer member 638. The outer member 638 can be made of an optically-opaque material such as a polymer-based coating or sleeve, for example, and can include a window or transmissive portion 646 through which the laser energy can be transmitted during a surgical procedure. A reflective member 640 including a multilayer dielectric coating 641 on an angled surface 641, a distal end portion of a buffer layer 630, a distal end portion of a cladding layer 632, and an optical-fiber-core distal end portion 634 can be disposed within the capillary 636. A proximal end portion of an inner surface of the capillary 636 can be coupled to an outer surface of the distal end portion of the buffer layer 630.

Grooves 658 can be defined in the outer surface of the buffer layer 630 to increase the total surface area of the outer surface of the buffer layer 630 that overlaps the capillary 636. The grooves 658 can be made by, for example, a thermal process that defines the number, size, shape, and/or spacing of the grooves 658. An adhesive 656 can be applied to the grooved surface portion of the buffer layer 630 to couple the grooved surface portion to the inner surface of the capillary 636.

In another embodiment, as shown in FIG. 6B, a grooved surface of the buffer layer 670 of a side-firing optical-fiber 654 can be coupled to a proximal end portion of an inner surface of a capillary 676 and to a proximal end portion of a protective cap or outer member 678. A reflective member 680, a distal end portion of the buffer layer 670, a distal end portion of a cladding layer 672, and an optical-fiber-core distal end portion 674 can be disposed within the capillary 636 along centerline 677. Reflective member 680 can include a multilayer dielectric coating 681 on an angled surface 682. The grooves 698 can be made by, for example, a thermal process that defines an appropriate number, size, shape, and/or spacing for the grooves. An adhesive 696 can be applied to the grooved surface portion of the buffer layer 670 to couple the grooved surface portion to the inner surface of the capillary 676 and to the outer member 678.

In some embodiments, a first portion of the grooved surface portion of the buffer layer 670 can be used to couple the buffer layer 670 to the capillary 676 and a second portion of the grooved surface portion of the buffer layer 670 can be used to couple the buffer layer 670 to the outer member 678. In this regard, the same or different adhesives can be used to couple the first portion of the grooved surface portion and the second portion of the grooved surface portion of the buffer layer 670 to the capillary 676 and the outer member 678, respectively. For example, a first adhesive can be used to couple the grooved surface portion to a sapphire-based capillary 676 and a second adhesive can be used to couple the grooved surface portion to a polymer-based outer member 678. In some embodiments, the grooves in the first portion of the grooved surface portion may be different in size, shape, spacing, and/or number than those in the second portion of the grooved surface portion.

FIGS. 7A-7B are cross-sectional views of a grooved buffer layer surface coupled to a capillary with an optically-opaque protective cap, according to embodiments of the invention. FIG. 7A shows a side-firing optical-fiber distal end portion 716 that includes a capillary 736 disposed within a high-profile protective cap or outer member 738. The outer member 738 can be made of an optically-opaque material such as surgical-grade stainless steel, for example, and can include a window or transmissive portion 746 through which the laser energy can be transmitted during a surgical procedure. A reflective member 740, a distal end portion of a buffer layer 730, a distal end portion of a cladding layer 732, and an optical-fiber-core distal end portion 734 can be disposed within the capillary 736. A proximal end portion of an inner surface of the capillary 736 can be coupled to an outer surface of the distal end portion of the buffer layer 730.

Grooves 758 can be defined in the outer surface of the buffer layer 730 to increase the total surface area of the outer surface of the buffer layer 730 that overlaps the capillary 736. The grooves 758 can be made by, for example, a thermal process that defines the number, size, and/or spacing of the grooves 758. An adhesive 756 can be applied to the grooved surface portion of the buffer layer 730 to couple the grooved surface portion to the inner surface of the capillary 736.

In another embodiment, as shown in FIG. 7B, a grooved surface portion of the buffer layer 770 can be coupled to a proximal end portion of an inner surface of a capillary 776 and to a proximal end portion of a protective cap or outer member 778. The grooves 798 can be made by, for example, a thermal process that defines an appropriate number, size, shape, and/or spacing for the grooves. An adhesive 796 can be applied to the grooved surface portion of the buffer layer 770 to couple the grooved surface portion to the inner surface of the capillary 776 and to the outer member 778.

In some embodiments, a first portion of the grooved surface portion of the buffer layer 770 can be used to couple the buffer layer 770 to the capillary 776 and a second portion of the grooved surface portion of the buffer layer 770 can be used to couple the buffer layer 770 to the outer member 778. In this regard, the same or different adhesives can be used to couple the first portion of the grooved surface portion and the second portion of the grooved surface portion of the buffer layer 770 to the capillary 776 and the outer member 778, respectively. For example, a first adhesive can be used to couple the grooved surface to a sapphire-based capillary 776 and a second adhesive can be used to couple the grooved surface to a metal-based outer member 778. In some embodiments, the grooves in the first portion of the grooved surface portion may be different in size, shape, spacing, and/or number than those in the second portion of the grooved surface portion.

Figure 8:
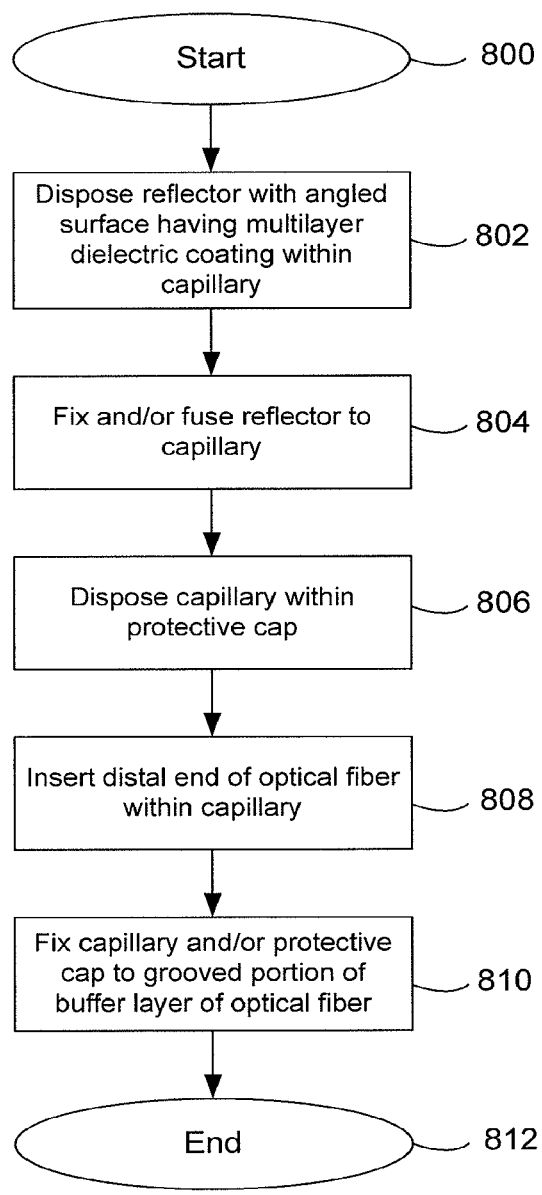
FIGS. 8-9 are flow charts illustrating a method according to an embodiment of the invention.

FIG. 8 is a flow chart illustrating a method for manufacturing a side-firing optical fiber, according to an embodiment of the invention. At 802, after start 800, a reflective member or reflector can be disposed within a capillary. A multilayer dielectric coating can be disposed on a proximal end surface of a reflector. The proximal end surface of the reflector can be angled relative to a longitudinal axis or centerline of a distal end portion of a capillary. The reflector can be positioned such that the distal end surface of the reflector is proximate to a distal end of an inner portion of the capillary. The distal end surface of the reflector can be, for example, substantially perpendicular to the longitudinal axis or centerline of the distal end portion of the capillary.

At 804, the reflector can be fixedly coupled to the capillary. For example, a laser can be used to fuse a portion of an outer surface of the reflector that is offset from the longitudinal axis or centerline of the distal end portion of the capillary to an inner portion of the capillary. In another example, a laser can be used to fuse a portion of the distal end surface of the reflector to an inner portion of the capillary. In yet another example, a laser can be used to fuse a portion of the distal end surface of the reflector and a portion of an outer surface of the reflector to an inner portion of the capillary.

At 806, the capillary can be disposed within a protective cap. In an embodiment, the protective cap can be a low-profile member made of a polymer-based coating or sleeve, for example. In another embodiment, the protective cap can be a high-profile member made of a metal such as stainless steel, for example. In some embodiments, the capillary can be disposed within the protective cap before the reflector is disposed within the capillary and/or fixedly coupled within the capillary. At 808, a distal end portion of an optical fiber can be disposed within the capillary. A distal end of the optical fiber core and the coated reflector can be collectively configured to redirect laser energy in a side-fired direction that is offset from the longitudinal axis of the distal end portion of the capillary.

At 810, the proximal end portion of the capillary can be coupled to an outer surface of a buffer layer of the optical fiber. The overlap between the capillary and the outer surface of the buffer layer may need to be sufficiently large to provide mechanical stability to the coupling. Grooves can be defined in the outer surface of the buffer layer to increase the total surface area of the outer surface of the buffer layer that overlaps the capillary. The grooves in the grooved surface portion of the buffer layer can be made by, for example, a thermal process that defines an appropriate number, size, and/or spacing for the grooves. An adhesive can be applied to the grooved surface portion of the buffer layer to couple the grooved surface portion with the inner portion of the capillary. In another embodiment, the grooved surface portion of the buffer layer can be coupled to the proximal end of the outer member. After 810, the method can proceed to end 812.

Figure 9:
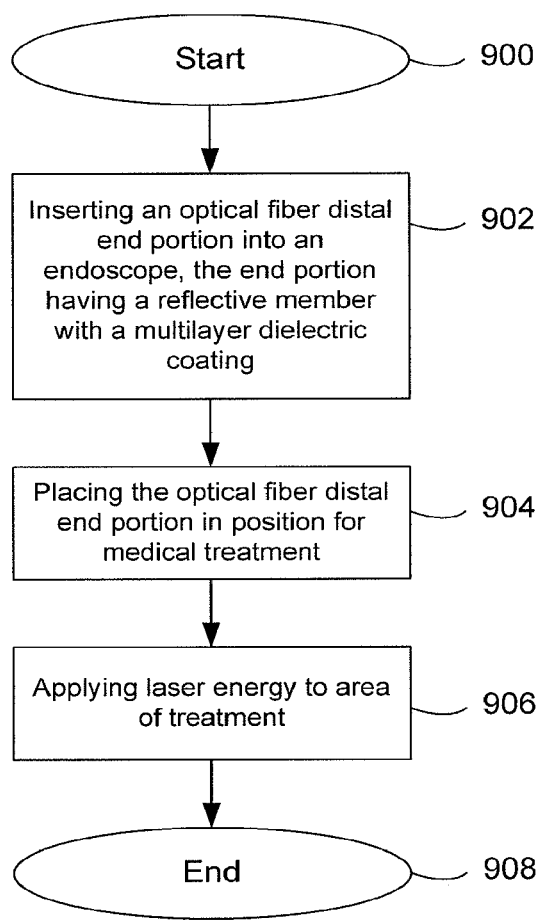

FIG. 9 is a flow chart illustrating a method of using an optical fiber side-firing system, according to another embodiment of the invention. At 902, after start 900, an optical-fiber distal end portion can be inserted within an inner portion or lumen of an endoscope. The optical-fiber distal end portion includes a reflector inside a capillary and a multilayer dielectric coating on an angled surface of the reflector. The optical fiber and the capillary can be coupled through a grooved surface portion of a buffer layer of the optical fiber. At 904, the endoscope can be at least partially inserted into the patient's body during a laser-based surgical procedure. Once inserted into the patient's body, the endoscope can be used to place or position the optical-fiber distal end portion at or near the area of treatment. At 906, laser energy from a laser source can be transmitted through the optical fiber such that laser energy is side-fired or laterally redirected to the treatment area. After 906, the method can proceed to end 908.

CONCLUSION

While various embodiments have been described above, it should be understood that they have been presented by way of example only, and not limitation. For example, the optical fiber side-firing system described herein can include various combinations and/or sub-combinations of the components and/or features of the different embodiments described. Although described with reference to use for treatment of symptoms related to BPH, it should be understood that the optical fiber side-firing system and the side-firing optical fibers, as well as the methods of using the optical fiber side-firing system and the side-firing optical fibers can be used in the treatment of other conditions.

Embodiments of a side-firing optical fiber can also be provided without the optical fiber side-firing system described herein. For example, a side-firing optical fiber can be configured to be used with other laser sources, endoscopes, etc., not specifically described herein. A side-firing optical fiber can have a variety of different shapes and sizes than as illustrated and described herein. A side-firing optical fiber can also include other features and/or components such as, for example, lenses and/or filters.

In one embodiment, an apparatus can include a capillary, a reflector, and an optical fiber. The capillary can have a distal end portion. The reflector can be disposed within the capillary. The reflector can have a surface angled relative to a longitudinal axis of the distal end portion of the capillary. The angled surface can be configured to redirect laser energy in a lateral direction offset from the longitudinal axis. The optical fiber can have a buffer layer. An outer surface of a distal end portion of the buffer layer can define a grooved surface portion of the buffer layer having multiple grooves. The grooved surface portion of the buffer layer can be fixedly coupled to the capillary. The grooved surface portion of the buffer layer can be defined based on a shape, a size, a number, and/or a spacing of a groove from the multiple grooves.

In some instances, the apparatus can also include a multilayered dielectric coating disposed on the angled surface of the reflector. The multilayer dielectric coating and the angled surface can be collectively configured to redirect laser energy in a lateral direction offset from the longitudinal axis. The reflector can be fused to the capillary, for example. The apparatus can also include a member that can be configured to be inserted into a patient's body. The capillary can be disposed within the member, for example. The member can include a coating that can be disposed about at least a portion of the capillary. The member can be made of a ceramic, a sapphire, and/or a stainless steel, for example. The member can be fixedly coupled to the grooved surface portion of the buffer layer.

In another embodiment, a method can include disposing a reflector within a capillary, defining (e.g., thermally) a grooved surface portion of a buffer layer, and fixedly coupling the grooved surface portion of the buffer layer to the capillary. The reflector can have a surface angled relative to a longitudinal axis of a distal end portion of the capillary. The reflector can include a multilayered dielectric coating. The grooved surface portion of a buffer layer can have multiple grooves on an outer surface of the buffer layer of a distal end portion of an optical fiber. The defining of the grooved surface portion can include defining a shape, a size, a number, and/or a spacing of a groove from the multiple of grooves.

The method can include disposing the distal end portion of the optical fiber into an interior of the capillary before fixedly coupling the grooved surface portion of the buffer layer to the capillary. In some instances, after the disposing of the reflector, the method can include fusing the reflector to the capillary. Before fixedly coupling the grooved surface portion of the buffer layer to the capillary, the method can include applying an adhesive to the grooved surface portion of the buffer layer.

Moreover, the method can include disposing the capillary within a member configured to be inserted into a patient's body and/or fixedly coupling the grooved surface portion of the buffer layer to a member configured to be inserted into a patient's body.

Disposing the reflector within the capillary can include disposing the angled surface of the reflector such that laser energy can be redirected from the distal end of the optical fiber to a transmissive portion of a member configured to be inserted into a patient's body when laser energy is sent to the optical fiber.

In another embodiment, a method can include disposing a first member within a second member. The first member can have a surface angled relative to a longitudinal axis of a distal end portion of the second member. The angled surface can include a multilayered dielectric coating, for example. The angled surface can be configured to redirect laser energy in a lateral direction offset from the longitudinal axis. The method can also include defining a grooved surface portion of a buffer layer having multiple grooves on an outer surface of the buffer layer of a distal end portion of an optical fiber and fixedly coupling the grooved surface portion of the buffer layer to the second member. The defining of the grooved surface portion of the buffer layer can include defining a shape, a size, a number, and/or a spacing of a groove from the multiple grooves.

After disposing the first member within the second member, the method can include fusing the first member to the second member. Moreover, an adhesive can be applied to the grooved surface portion of the buffer layer before fixedly coupling the grooved surface portion of the buffer layer to the second member. The second member can be disposed within an outer member configured to be inserted into a patient's body.

In some instances, the method can include fixedly coupling the grooved surface portion of the buffer layer to an outer member configured to be inserted into a patient's body.

Disposing first member within the second member can include disposing the angled surface of the first member such that laser energy is redirected from the distal end of the optical fiber to a transmissive portion of an outer member configured to be inserted into a patient's body when laser energy is sent to the optical fiber.

What is claimed is:

1. A side-firing optical fiber apparatus, comprising:
a capillary having a distal end portion;
a reflector disposed within the distal end portion of the capillary, the reflector having a surface angled relative to a longitudinal axis of the distal end portion of the capillary, the angled surface including alternating layers of two or more materials each with different dielectric constants and configured to redirect laser energy in a lateral direction offset from the longitudinal axis;
an optical fiber terminating in a distal end face and having a buffer layer fixedly coupled to the capillary, the distal end face of the optical fiber extending along an axis perpendicular to the longitudinal axis of the distal end portion of the capillary; and
a member extending proximally of a proximal end face of the capillary, wherein the member includes a portion wrapping around the proximal end face of the capillary, and wherein the portion of the member wrapping around the proximal end face of the capillary is coupled to a portion of the buffer layer having a plurality of grooves via adhesive;
wherein a distal facing surface of the reflector is fused to the capillary.

2. The apparatus of claim 1, wherein the member is configured to be inserted into a patient's body, the capillary being disposed within the member.

3. The apparatus of claim 1, wherein the member is configured to be inserted into a patient's body, the member including a coating disposed about at least a portion of the capillary.

4. The apparatus of claim 1, wherein the member is configured to be inserted into a patient's body, the member being made of at least one of a ceramic, a sapphire, or a stainless steel, the capillary being disposed within the member.

5. The apparatus of claim 1, wherein a circumferential surface of the reflector is fused to the capillary.

6. The apparatus of claim 1, wherein the capillary further includes a proximal end portion coupled to the portion of the buffer layer including the plurality of grooves.

7. The apparatus of claim 6, wherein the proximal end portion of the capillary and the portion of the member wrapping around the proximal end face of the capillary are coupled to the portion of the buffer layer having the plurality of grooves via adhesive.

8. A side-firing optical fiber apparatus, comprising:
a capillary having a proximal end portion and a distal end portion;
a reflector disposed within the distal end portion of the capillary and having a thermal expansion coefficient matching a thermal expansion coefficient of the capillary, the reflector further having a surface angled relative to a longitudinal axis of the distal end portion of the capillary, the angled surface configured to redirect laser energy in a lateral direction offset from the longitudinal axis, the angled surface including alternating layers of two or more materials each with different dielectric constants;
an optical fiber terminating in a distal end face and having a buffer layer fixedly coupled to the capillary, the distal end face of the optical fiber extending along an axis perpendicular to the longitudinal axis of the distal end portion of the capillary; and
a member extending proximally of a proximal end face of the capillary, wherein the member includes a portion extending along an axis parallel with the longitudinal axis, and a proximalmost end of the member extending along an axis angled with respect to the axis of the portion of the member, wherein the proximalmost end of the member extending along an axis angled with respect to the axis of the portion of the member is coupled to a portion of the buffer layer having a plurality of grooves;
wherein a distal facing surface of the reflector is fused to the capillary, and wherein the proximal end portion of the capillary is coupled to the portion of the buffer layer having the plurality of grooves.

9. The apparatus of claim 8, wherein the member is configured to be inserted into a patient's body, the capillary being disposed within the member.

10. The apparatus of claim 8, wherein the member is configured to be inserted into a patient's body, the member including a coating disposed about at least a portion of the capillary.

11. The apparatus of claim 8, wherein the member is configured to be inserted into a patient's body, the member being made of at least one of a ceramic, a sapphire, or a stainless steel, the capillary being disposed within the member.

12. The apparatus of claim 8, wherein a circumferential surface of the reflector is fused to the capillary.

13. The apparatus of claim 8, wherein the proximalmost end of the member extending along an axis angled with respect to the axis of the portion of the member is coupled to the portion of the buffer layer having a plurality of grooves via adhesive.

14. A side-firing optical fiber apparatus, comprising:
a capillary having a proximal end portion and a distal end portion;
a reflector disposed within the distal end portion of the capillary, the reflector having a surface angled relative to a longitudinal axis of the distal end portion of the capillary;
an optical fiber terminating in a distal end face and having a buffer layer fixedly coupled to the capillary, the buffer layer including a portion having a plurality of grooves, the distal end face of the optical fiber extending along an axis perpendicular to the longitudinal axis of the distal end portion of the capillary; and
a member extending proximally of a proximal end face of the capillary, wherein the member includes a portion wrapping around the proximal end face of the capillary, wherein the portion of the member wrapping around the proximal end face of the capillary and the proximal end portion of the capillary are coupled to the portion of the buffer layer having the plurality of grooves.

15. The apparatus of claim 14, wherein a distal facing surface of the reflector is directly fused to the capillary.

16. The apparatus of claim 14, wherein a circumferential surface of the reflector is directly fused to the capillary.

17. The apparatus of claim 14, wherein the proximal end portion of the capillary and the portion of the member wrapping around the proximal end face of the capillary are coupled to the portion of the buffer layer having the plurality of grooves via adhesive.

18. The apparatus of claim 14, wherein the portion of the member wrapping around the proximal end face of the capillary is coupled to a first subset of grooves of the plurality of grooves, and wherein the proximal end portion of the capillary is coupled to a second subset of grooves of the plurality of grooves, wherein at least one of a size, a shape, a spacing, or a number of the first plurality of grooves is different than at least one of a size, a shape, a spacing, or a number of the second plurality of grooves.

* * * * *